(12) United States Patent
Kishimoto et al.

(10) Patent No.: US 8,618,078 B2
(45) Date of Patent: Dec. 31, 2013

(54) FOODS AND DRINKS HAVING HEALTH BENEFITS AND METHOD FOR ADDING HEALTH BENEFITS TO FOODS AND DRINKS

(75) Inventors: Yuka Kishimoto, Sanda (JP); Hiroshi Oga, Kawanisi (JP); Noriko Kitamura, Takarazuka (JP)

(73) Assignee: Matsutani Chemical Industry Co., Ltd., Hyogo-ken (JP)

( * ) Notice: Subject to any disclaimer, the term of this patent is extended or adjusted under 35 U.S.C. 154(b) by 432 days.

(21) Appl. No.: 12/479,637

(22) Filed: Jun. 5, 2009

(65) Prior Publication Data

US 2009/0239823 A1    Sep. 24, 2009

Related U.S. Application Data

(62) Division of application No. 11/097,082, filed on Apr. 4, 2005, now abandoned.

(30) Foreign Application Priority Data

Apr. 2, 2004   (JP) .................. 2004-110159

(51) Int. Cl.
   *A61K 31/715* (2006.01)
(52) U.S. Cl.
   USPC .............................. 514/58; 424/439; 424/442
(58) Field of Classification Search
   USPC ......................................................... 514/58
   See application file for complete search history.

(56) References Cited

U.S. PATENT DOCUMENTS

| | | | |
|---|---|---|---|
| 5,344,824 A | 9/1994 | Ohkuma et al. | |
| 5,380,717 A | 1/1995 | Ohkuma et al. | |
| 5,410,035 A | 4/1995 | Wakabayashi et al. | |
| 5,519,011 A | 5/1996 | Wakabayashi et al. | |
| 5,620,873 A | 4/1997 | Ohkuma et al. | |
| 6,495,190 B1 | 12/2002 | Yaginuma et al. | |
| 6,514,546 B2 | 2/2003 | Tsukuda et al. | |
| 2004/0197453 A1 | 10/2004 | Hirao et al. | |
| 2005/0220845 A1 | 10/2005 | Kishimoto et al. | |
| 2007/0166446 A1 * | 7/2007 | Boursier ....................... | 426/549 |

FOREIGN PATENT DOCUMENTS

| | | | |
|---|---|---|---|
| EP | 0 368 451 A2 | 5/1990 | |
| EP | 0 444 891 A1 | 9/1991 | |
| EP | 0 561 090 A1 | 9/1993 | |
| EP | 0 593 368 A1 | 4/1994 | |
| JP | 2-145169 A | 6/1990 | |
| JP | 02-154664 A | 6/1990 | |
| JP | 03-244364 A | 10/1991 | |
| JP | 03-244365 A | 10/1991 | |
| JP | 03-247258 A | 11/1991 | |
| JP | 5-214002 A | 8/1993 | |
| JP | 6-166622 A | 6/1994 | |
| JP | 7-28693 B2 | 4/1995 | |
| JP | 7-28694 B2 | 4/1995 | |
| JP | 7-28695 B2 | 4/1995 | |
| JP | 7-45521 B2 | 5/1995 | |
| JP | 10-150934 A | 6/1998 | |
| JP | 11-116602 A | 4/1999 | |
| JP | 2001-346522 A | 12/2001 | |
| JP | 2002-330735 A | 11/2002 | |
| JP | 2003-164272 A | 6/2003 | |
| WO | 03/007734 A1 | 1/2003 | |
| WO | WO 2005/079584 * | 2/2005 | .............. A21D 2/18 |

OTHER PUBLICATIONS

Mendel (Some Relations of Diet to Fat Deposition in the Body, Tale Journal of Biology and Medicine, vol. 3, No. 2, 1930).*
"Lipid metabolism", Medical Dictionary, Nanzando, Jan. 16, 1998, p. 852-853.

* cited by examiner

*Primary Examiner* — Frederick Krass
*Assistant Examiner* — Adam C Milligan
(74) *Attorney, Agent, or Firm* — Sughrue Mion, PLLC

(57) ABSTRACT

A method for controlling intestinal function, blood sugar level, body fat or serum lipid, or maintaining and improving glucose tolerance. The method comprises giving to human body or animal foods and drinks, having health benefits, or enriched with health benefits, wherein the foods and drinks comprise as an active ingredient a hydrogenated, indigestible dextrin that is obtained by digesting pyrodextrin with an enzyme to obtain an indigestible dextrin, and then hydrogenating the indigestible dextrin.

2 Claims, 4 Drawing Sheets

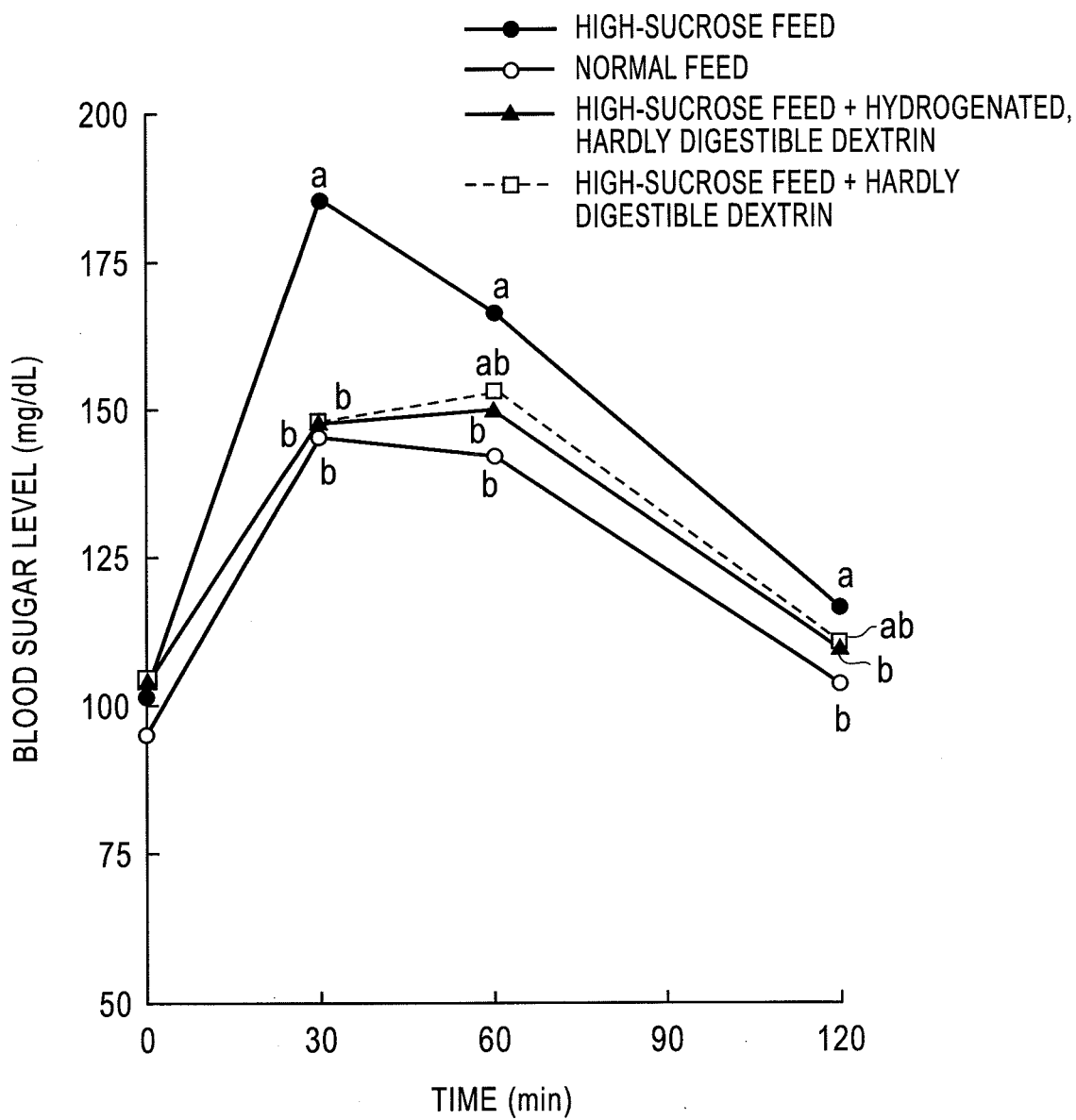

FOODS AND DRINKS HAVING HEALTH BENEFITS AND METHOD FOR ADDING HEALTH BENEFITS TO FOODS AND DRINKS

CROSS REFERENCE TO RELATED APPLICATION

This is a division of U.S. patent application Ser. No. 11/097,082 filed Apr. 4, 2005, the entire disclosure of which is hereby incorporated by reference.

TECHNICAL FIELD

The present invention relates to a method for adding health benefits (health claims) to foods or drinks, or for increasing the health benefits by adding a hydrogenated, hardly digestible dextrin (resistant maltodextrin) obtainable by hydrogenating hardly digestible dextrin to reduce carbonyl group thereof, to foods or drinks by partially or wholly replacing food components with the hydrogenated, hardly digestible dextrin, and to the foods and drinks obtainable by this method.

BACKGROUND ART

Recently, as the dietary habits are being westernized and also living habits are being changed in Japan, patients suffering from diseases caused by the living habits such as diabetes, hyperlipemia, hypertension and obesity are increasing in number. For the purpose of preventing people from these diseases, the demand of various healthful foods such as Foods for Specified Health Use is increasing and, in addition, the physiological function or action of foods has lately attracted attention. Dietary fibers known to have physiological actions such as controlling action of intestinal function and also controlling action of postprandial hyperglycemia are generally used as materials for improving the function of foods.

The dietary fibers can be divided into two groups, i. e. water-soluble dietary fibers and water-insoluble ones. These two groups of dietary fibers are different from each other in the physical properties and physiological properties. Because the water-insoluble dietary fibers such as cellulose and hemicellulose are difficultly assimilated in the large intestine and these fibers containing water are excreted in feces, the fibers exhibit physiological actions of increasing the quantity of the feces and shortening the passing time in the gastrointestinal tracts. The water-soluble dietary fibers can be classified into a group of those which exhibit a high viscosity when they are dissolved in water, such as pectin, psyllium and guar gum and a group of those which are not viscous when they are dissolved in water, such as hardly digestible dextrin and polydextrose. The water-soluble dietary fibers having a high viscosity form a gel in the digestive tracts to retard the absorption of nutrients by the inhibition of the diffusion. For example, when the absorption of saccharides is retarded, an increase in the blood sugar level can be controlled and, accordingly, excess secretion of insulin can be effectively prevented. When the blood sugar level and insulin secretion after meals can be controlled, it is expected to improve the glucose tolerance and also the lipid metabolism in the long run. Further, when the lipid absorption is retarded, the elevation of neutral fat level after meals is controlled to exert an influence on the lipid metabolism. In addition, the discharge of bile acid is promoted by the shortening in the passing time in the digestive tracts and increase in quantity of feces. The effects thus obtained are that the sterol group in the body is reduced and that cholesterol level in the serum is lowered. However, it is difficult to add an effective amount of highly viscous dietary fibers to foods because such an additive exerts an influence on the taste, texture, shape, etc. of the foods. Thus, the foods in which the dietary fibers can be added are limited.

On the other hand, as the water-soluble dietary fibers of a low viscosity, hardly digestible dextrin (dietary fiber-containing dextrin) produced from starch is known. Patent Document 1 discloses a method for producing hardly digestible dextrin by reacting pyrodextrin with α-amylase. Patent Document 2 discloses a method for producing dextrin having a high dietary fiber content by reacting pyrodextrin with α-amylase and then with glucoamylase and then collecting the dietary fibers by the chromatographic fractionation and also a method for increasing the dietary fiber content by the reaction with transglucosidase prior to the chromatographic fractionation. Because the physical properties of the hardly digestible dextrin are suitable for the additives for foods, this kind of dextrin is widely used as dietary fiber material for foods. The physiological actions of the hardly digestible dextrin include, for example, controlling actions of intestinal function (refer to Patent Document 3), preventing action from obesity or glucose tolerance troubles by the addition thereof to foods such as sugar (Patent Document 4), controlling action of insulin secretion (Patent Document 5), lowering action of serum lipid component content (Patent Document 6) and lowering action of high blood pressure (Patent Document 7). The hardly digestible dextrin is used for healthful foods such as Foods for Specified Health Use.

However, the hardly digestible dextrin is colored by the roasting at a high temperature in the course of the steps of producing it. Although it can be decolored to some extent in a purification step, the complete decoloration is difficult and the final commercial product thereof is in the form of pale yellow powder. Thus, when the hardly digestible dextrin is added to foods such as those the coloring of which causes a problem, e.g. water, transparent soft drinks and rice, the foods are colored to lower the commercial value of them. For this reason, the amount of the hardly digestible dextrin is limited. It was thus difficult to use the hardly digestible dextrin in such an amount that the physiological function thereof can be expected. Although the hardly digestible dextrin can be added to foods having a deep color such as tea drinks, soups and miso soup without any problem immediately after the production, the foods are gradually colored brown with time to damage the stability of the appearance of these commercial products. Another problem is that when the hardly digestible dextrin is used in combination with other sweetening agents, the foods having a neutral pH are easily browned in the course of the production thereof and, in addition, the foods are easily scorched in the course of the boiling down.

On the other hand, Patent Document 8 discloses hardly digestible starch syrup or powdered starch syrup obtained by hydrolyzing pyrodextrin in the presence of an acid has a physiological action and that such a syrup can be boiled down and is usable for foods in a wide range. However, the hardly digestible starch syrup or powdered starch syrup has a high saccharide content and, accordingly, it has a high degree of sweetness. Thus, such syrup cannot be used for saccharide-free foods or foods which must have no sweetness, while it can be added to foods which contain saccharides.

For solving the problem of the coloring of hardly digestible dextrin and increase in the degree of coloring thereof with time, it is known to hydrogenate the reducing end thereof because the coloring is caused by Maillard reaction (browning). When the reducing end is sealed, the hardly digestible dextrin cannot react with amino acids and, therefor, Maillard reaction does not occur. This technique is well known and, in fact, hydrogenated dextrin obtained by hydrogenating dextrin (refer to Patent Document 9), hydrogenated, hardly digestible starch syrup obtained by hydrogenating the hardly digestible starch syrup (refer to Patent Document 10), etc. are known. After the hydrogenation, dextrin thus hydrogenated has a lowered calorie and the digestion and absorption thereof are slowed down. However, when the hydrogenated dextrin is taken in together with other saccharides, it does not exert any influence on the digestion and absorption of these saccharides. Other physiological functions of the hydrogenated dextrin have not yet been confirmed. As for the hardly digestible starch syrup, only its non-cariogenic function was confirmed but other physiological functions thereof have not yet been elucidated. It is also known that hydrogenated, hardly digestible dextrin obtained by hydrogenating the hardly digestible dextrin is free from the change in color with time and that this dextrin has a refreshing taste. However, the health benefit of this hydrogenated, hardly digestible dextrin has not yet been elucidated (Patent Documents 1 and 2).

Under the above-described circumstances, it is expected to develop and also to commercialize a hardly digestible substance free from the above-described defects of the hardly digestible dextrin, capable of being added to any kind of foods without the problem of the coloring, and having physiological functions equal to or better than various physiological functions of the hardly digestible dextrin.

[Patent Document 1] Japanese Patent Kokai No. Hei 2-145169
[Patent Document 2] Japanese Patent Kokai No. Hei 2-154664
[Patent Document 3] Japanese Patent No. 2007645
[Patent Document 4] Japanese Patent Kokai No. Hei 6-166622
[Patent Document 5] Japanese Patent No. 2007644
[Patent Document 6] Japanese Patent No. 2007646
[Patent Document 7] Japanese Patent No. 2019839
[Patent Document 8] Japanese Patent Kokai No. Hei 11-116602
[Patent Document 9] Japanese Patent Kokai No. Hei 5-214002
[Patent Document 10] Japanese Patent Kokai No. Hei 10-150934

DISCLOSURE OF THE INVENTION

Problems to be Solved by the Invention

The object of the present invention is to develop foods and drinks having health benefits such as controlling action of intestinal function, controlling action of the blood sugar level, maintaining and improving action of glucose tolerance, controlling action of serum lipid and controlling action of body fat. Another object of the present invention is to provide a method for adding the health benefits to foods and drinks or increasing health benefits in foods and drinks.

Means for Solving the Problem

The inventors found that a health benefit such as controlling action of intestinal function action, controlling action of serum lipid, controlling action of body fat, maintaining and improving action of glucose tolerance, or controlling action of blood sugar level can be added to foods and drinks by using a hydrogenated, hardly digestible dextrin obtainable by digesting pyrodextrin with an enzyme and then hydrogenating the digested dextrin as at least a part of constituents of foods and drinks. The present invention has been completed on the basis of this finding.

Namely, in the first aspect of the invention, the present invention provides foods and drinks, having health benefits, or enriched with health benefits, comprising as an active ingredient a hydrogenated, hardly digestible dextrin obtainable by digesting pyrodextrin with an enzyme and then hydrogenating the digested dextrin. In the second aspect of the invention, the present invention provides foods and drinks, having health benefits, or enriched with health benefits according to the first aspect of the invention, wherein the health benefit is at least one member selected from the group consisting of controlling action of intestinal function, controlling action of blood sugar level, maintaining and improving action of glucose tolerance, controlling action of body fat and controlling action of serum lipid. In the third aspect, the present invention provides an agent for controlling intestinal functions as foods and drinks, an agent for controlling blood sugar level as foods and drinks, an agent for maintaining and improving glucose tolerance as foods and drinks, an agent for controlling body fat as foods and drinks, or an agent for controlling serum lipid as foods and drinks, which comprises the hydrogenated, hardly digestible dextrin as the active ingredient. In the fourth aspect, the present invention provides a method for adding health benefits to foods and drinks or for increasing the health benefits in foods and drinks, which comprises the steps of adding at least 3 g/meal or 3 g/day, in terms of hardly digestible components, of the hydrogenated, hardly digestible dextrin to foods or drinks according to the first aspect of the present invention to foods or drinks, or replacing at least a part of the foods or drinks with the hydrogenated, hardly digestible dextrin according to the first aspect of the present invention.

Effect of the Invention

According to the present invention, extremely excellent healthful foods can be provided because the health benefits can be added to foods and drinks or the health benefits of them can be increased without impairing the essential properties and characteristics of the foods. Further, according to the present invention, it is possible to obtain foods and drinks containing the hardly digestible substance soluble in water which substance is capable of forming a stable white powder or colorless transparent aqueous solution having various health benefits, free from coloring foods when the substance is added to the foods, and free from browning with time.

BEST MODE FOR CARRYING OUT THE INVENTION

The term "health benefits" used herein means that when a food containing the hydrogenated, hardly digestible dextrin used in the present invention is taken, at least one of controlling action of blood sugar level, controlling action of serum lipid, controlling action of body fat, maintaining and improving action of glucose tolerance and controlling action of intestinal function is achieved. The term "controlling action of blood sugar level" used herein means a controlling action of the elevation of blood sugar level after meals or a lowering action of a high fasting blood sugar level after taking foods containing carbohydrates. The term "controlling action of serum lipid" used herein means such an action that when foods which elevate the serum cholesterol level and serum neutral fat level are repeatedly taken for a long period of time, the elevation of the level is controlled or the elevated serum fat level is lowered. The term "controlling action of body fat" used herein means such an action that when foods which elevate the body fat level are repeatedly taken for a long period of time, the elevation of the body fat level is controlled or the elevated body fat level is lowered. The term "maintaining and improving action of glucose tolerance" used herein means such an action that when foods, which lower the glucose tolerance (a function of maintaining the normal blood sugar level) after taking for a long period of time, are repeatedly taken, the lowering of the glucose tolerance is prevented or the lowered glucose tolerance is enhanced.

The hydrogenated, hardly digestible dextrin used in the present invention is obtainable by reducing a hardly digestible dextrin containing preferably at least 45% by weight, more preferably at least 60% by weight and most preferably 85 to 95% by weight, of hardly digestible components as determined by a high performance liquid chromatographic method (enzyme—HPLC method) which is a method for analyzing dietary fibers as described in Ei-Shin No. 13 (analytical methods, etc. of nutrient components in the nutrition indication standard). Generally, the hydrogenated, hardly digestible dextrin can be obtained by digesting pyrodextrin with an enzyme to remove the digestible part thereof and then reducing the obtained hardly digestible dextrin by the hydrogenation.

The hydrogenated, hardly digestible dextrin can be prepared by a well known method such as a method described in Japanese Patent Kokai No. Hei 2-154664. In this method, starch is heat-treated to obtain pyrodextrin, the pyrodextrin is hydrolyzed with an enzyme and then the obtained product is reduced by the hydrogenation to obtain he hydrogenated, hardly digestible dextrin. The heat treatment of starch is preferably conducted in the presence of an acid. For the hydrolysis of the obtained pyrodextrin, α-amylase can be used alone or in combination with glucoamylase. In the latter case, it is preferred to use α-amylase followed by glucoamylase. β-amylase is also usable in addition to these enzymes. β-amylase can be used alone or in combination with other enzymes. When two or three kinds of enzymes are used in combination, it is preferred to use α-amylase followed by glucoamylase or β-amylase. It is most preferred to use α-amylase followed by glucoamylase. Then hardly digestible dextrin containing preferably at least 45% by weight, more preferably at least 60% by weight and most preferably 85 to 95% by weight based on the solid, of the hardly digestible component can be separated and purified. The hardly digestible component of the obtained hardly digestible dextrin has a number average molecular weight of preferably 1000 to 3000, more preferably 1300 to 2500 and most preferably 2000.

The starch used as the starting material for the hydrogenated, hardly digestible dextrin in the present invention is not particularly limited. For example, starch obtained from corn, waxy corn, potato, tapioca, sweet potato, sago palm, wheat, barley and rice are usable. The detailed description on the method will be given below.

A mineral acid (such as hydrochloric acid or nitric acid) is added to the starch. Preferably, 3 to 10% by weight of 1 wt. % aqueous solution of hydrochloric acid is added to 100 parts by weight of starch. After the heat treatment, pyrodextrin can be obtained as an intermediate product. It is preferred that before the heat treatment, the aqueous solution of starch and mineral acid is stirred with a suitable mixer to obtain the homogeneous mixture and then aged and then water content of the obtained mixture is reduced to about 5% by weight by pre-drying the mixture at about 100 to 120° C. The heat treatment is conducted at 140 to 200° C. for 0.2 to 120 minutes, preferably 20 to 120 minutes. The higher the temperature of the heat treatment, the higher the hardly digestible component content of the intended product. However, because increase in quantity of the colored substance starts at around 180° C., the heat treatment temperature is preferably around 150° C.

It is possible to carry out the reaction at a high temperature in a short period of time by selecting a heating device. For example, when a device suitable for carrying out the uniform reaction in a short period of time, such as an extruder, is used, the heat treatment can be efficiently conducted. In the mass production of the product by the reaction of the powdery reactants, it is sometimes required to change the heating conditions. In such a case, it is desirable to suitably change the heating conditions, taking the quality of the product obtained after the heat treatment into consideration.

Then the pyrodextrin is dissolved in water to obtain a solution having a concentration of 20 to 50% by weight. pH of the solution is controlled at 5.5 to 6.5, preferably 6.0, with a neutralizing agent such as sodium hydroxide. 0.05 to 0.2% by weight of liquefying α-amylase is added to the reaction mixture and the hydrolysis is conducted at 80 to 95° C. (reaction temperature of α-amylase) usually for about 1 hour. Then the temperature is elevated to 120° C. to complete the enzymatic reaction of α-amylase. As the liquefying α-amylase, any of commercially available products is usable. They include, for example, Termamyl 120L (trade name of Novozyme Japan Co.).

If necessary, the liquid temperature is then lowered to 60° C., pH is controlled at 4 to 5, preferably 4.5 and 0.05 to 0.4 wt. % of glucoamylase is added thereto to carry out the hydrolysis at 55 to 60° C. for 4 to 48 hours, thereby to decompose the components, other than the hardly digestible components, into glucose. Then the temperature is elevated to 80° C. to complete the enzymatic reaction of glucoamylase. As the glucoamylase, any of commercially available products is usable. They include, for example, Gluczyme NL4.2 (trade name of Amano Enzyme Co.). Then the product is subjected to ordinary decolorization with active carbon, filtration, desalting and decolorization with an ion exchange resin and the product is concentrated to about 50% by weight.

The liquid product is then passed through a strongly acidic cation exchange resin column to separate the hardly digestible dextrin from the glucose-containing part by the chromatographic separation method. Thus, the hardly digestible dextrin containing preferably at least 45% by weight, more preferably at least 60% by weight and most preferably 85 to 95% by weight, based on the solids, of the hardly digestible component can be obtained.

In this case, the strongly acidic cation exchange resins are ordinary ones available on the market. Examples of preferred strongly acidic cation exchange resins include Amberlite IR-116, Amberlite IR-118, Amberlite IR-120B, XT-1022E and XT-471F (trade names of Japan Organo Co., Ltd.), Diaion SK-1B, Diaion SK102, Diaion SK104, Diaion SK106, Diaion SK110, Diaion SK112, Diaion SK116 and Diaion FR01 (trade names of Mitsubishi Chemical Industries Ltd.), and XFS-43281. 00, XFS-43280. 00, XSF-43279. 00 and XSF-43278. 00 (trade names of Dow Chemical Japan Ltd.). These resins are usually preferably converted into an alkali metal type or alkaline earth metal type before use. The flow rate is preferably in the range of SV=0.1 to 0.6. When the flow rate is not within this range, the workability and the separability are inclined to be deteriorated. In the course of the passage through the resin, the temperature of the liquid is preferably 20 to 70° C. When the temperature is lower than this range, the separability is lowered and the viscosity of the liquid is increased to impair the resin. On the other hand, when the temperature is higher than this range, the liquid is browned to lower the quality thereof and to deteriorate the resin.

Then the hardly digestible dextrin is reduced. This reduction (hydrogenation) reaction is carried out under the same conditions as ordinary reduction conditions of starch and saccharides. Usually, the hydrogenation reaction is carried out in the presence of an ordinary reduction catalyst such as Raney nickel, Raney cobalt or nickel diatomaceous earth under ordinary conditions, e. g. at a temperature of 50 to 150° C. under a hydrogen pressure of 50 to 130 kg/cm². It is preferred that hydrogen is dissolved in the solution until the saturation before the heating. When hydrogen supply is insufficient, undesirable side reactions such as oxidation and hydrolysis might occur. The hydrogenation is completed usually in 2 hours, though the time varies depending on the reaction conditions such as temperature and pressure. After the separation of the catalyst, the product is purified by an ordinary method such as re-decoloration with active carbon, filtration, desalting with an ion exchange resin or decoloration. The product is then concentrated and pulverized by spray-drying or the like or it is finally concentrated to about 70% by weight to obtain the liquid product.

For reference, a concrete method for preparing the hydrogenated, hardly digestible dextrin will be described below. The determination of the hardly digestible components and the number-average molecular weight thereof was conducted by the following method:

<Method for the Determination of Hardly Digestible Components>

The hardly digestible components in the hydrogenated, hardly digestible dextrin were determined by a high performance liquid chromatographic method (enzyme—HPLC method) which is a method for analyzing edible fibers as described in Ei-Shin No. 13 (on analytical methods, etc. of nutrient components in the nutrition indication standard).

<Determination of Number-Average Molecular Weight>

The number-average molecular weight was determined by the high performance liquid chromatography under the following conditions:

Columns: TSK gel G2500PWXL, G3000PWXL, G6000PWXL (products of Tosoh Corporation)
Detector: differential refractometer
Column Temperature: 80° C.
Flow rate: 0.5 ml/min
Mobile phase: distilled water
Amount of sample: 1% by weight, 100 µl As for the calculation of the molecular weight, the number-average molecular weight was determined from a calibration curve obtained using pullulan standard (having a known molecular weight), maltotriose and glucose as molecular weight markers, with Multi-station GPC-8020 (a product of Tosoh Corporation) according to the following formula:

$$Mn = \Sigma Hi / \Sigma (Hi/Mi) \times QF$$

Wherein Mn represents the number average molecular weight, Hi represents the height of the peak, Mi represents the molecular weight of pullulan, QF represents Q factor (Mark-Houwink coefficient).

[Referential Example]

Five hundred ppm of hydrochloric acid was added to commercially available corn starch. The obtained mixture was pre-dried to a water content of about 2 to 3% by weight with a flash dryer and then roasted with a rotary kiln at 140 to 145° C. for about 30 minutes to obtain pyrodextrin. Water was added to the pyrodextrin to a concentration of 30% by weight. Sodium hydroxide was added to the obtained mixture to adjust pH to 6. 0.2% by weight of Termamyl 120L (a product of Novozymes Japan) was added to the resulting mixture and the hydrolysis was carried out at 95° C. for 30 minutes. The reaction mixture was kept at 130° C. for 15 minutes to complete the enzymatic reaction. Then the reaction mixture was cooled to 60° C. and pH thereof was adjusted to 4.5. 0.3% by weight of Gluczyme NL4.2 (a product of Amano Enzyme Co.) was added thereto and the hydrolysis was carried out at 60° C. for 12 hours. The reaction mixture was kept at 80° C. for 30 minutes to complete the enzymatic reaction. After the desalting and decoloring by ordinary methods, the reaction mixture was concentrated to 50% by weight. The obtained solution was passed through a column filled with XFS-43279.00 (Dow Chemical Japan Ltd.) which is an alkali metal-type strongly acidic cation exchange resin at SV of 0.25. Then water was passed through the column to separate hardly digestible dextrin. The obtained solution was concentrated to 60% by weight and then placed in a reduction reaction vessel. Raney nickel R 239 (a trade name of Nikko Rica Corporation) as a catalyst was added thereto. Gaseous hydrogen was charged therein to a pressure of 100 kg/cm², and the reduction reaction was carried out under stirring at 400 to 600 rpm at 130° C. for 3 hours. The reduction reaction mixture was filtered to separate the catalyst. After the decolorization filtration through active carbon and desalting with an ion exchange resin, the product was concentrated and then pulverized by the spray drying to obtain hydrogenated, hardly digestible dextrin having a hardly digestible component content of 92% and a number-average molecular weight of the hardly digestible components of 2000.

Because carbonyl group in the sugar chain of the hydrogenated, hardly digestible dextrin thus obtained is reduced into hydroxyl group, this dextrin is hardly browned and excellent in the taste. In addition, its physicochemical stability and stability as the food are equivalent to those of the non-hydrogenated, hardly digestible dextrin. Powdery Fibersol 2H (trade name) and liquid Fibersol 2HL (trade name) sold by Matsutani Chemical Industry Co. Ltd., are usable as the hydrogenated, hardly digestible dextrin in the present invention. These two kinds of commercially available hydrogenated, hardly digestible dextrin are obtainable by the digestion with α-amylase and then with glucoamylase, followed by catalytic hydrogenation. They contain about 90% by weight, based on the solid, of hardly digestible components having a number-average molecular weight of about 2000.

As described above, the inventors found that foods and drinks containing hydrogenated, hardly digestible dextrin added thereto or foods and drinks partially replaced with the hydrogenated, hardly digestible dextrin exhibit various health benefits which contribute to the prevention of diseases caused by the living habits. The health benefits can be exhibited when the hydrogenated, hardly digestible dextrin content of the foods and drinks is preferably at least 3 g, more preferably at least 4 g, in terms of the hardly digestible components, per meal or each case of eating the foods and drinks. The amount of the hydrogenated, hardly digestible dextrin is at least 3 g/day, preferably at least 4 g/day, while it varies depending on the kind and form of the foods or drinks, and age, sex and body weight of the subject.

The foods usable in the present invention are not particularly limited. Examples of them include solid or liquid soft drinks, liquors, cakes, oily cakes, processed farm products, frozen sweets, bakeries, noodles, dairy products, pastas, chilled desserts, seasonings, pouch-packed or canned foods, processed meats, frozen processed meats, processed marine products, foods boiled in sweetened soy sauce, rice cakes, snacks and fast foods. Drinking water containing hydrogenated, hardly digestible dextrin is also included in the present invention. When these foods and drinks are taken, the functions of the present invention are exhibited. Also when the hydrogenated, hardly digestible dextrin of the present invention is directly taken together with foods and drinks, the functions of the present invention can also be exhibited.

It is particularly desirable to use a hydrogenated, hardly digestible dextrin obtainable by digesting pyrodextrin with α-amylase and glucoamylase and then hydrogenating the digested dextrin, which contains 85 to 95% by weight, in terms of solid components, of the hardly digestible components, and which has a number-average molecular weight of 2000. According to the present invention, the hydrogenated, hardly digestible dextrin thus obtained can be added to foods and drinks to have functional foods having the above-described functions. It is also preferred in the present invention to utilize this active ingredient as an agent for treating intestinal function and to be contained in foods and drinks; an agent for controlling blood sugar level and to be contained in foods and drinks, in particular, an agent for controlling the increase in blood sugar level after meal and to be contained in foods and drinks; an agent for maintaining glucose tolerance and to be contained in foods and drinks; an agent for controlling body fat and to be contained in foods and drinks; and an agent for controlling serum lipid and to be contained in foods and drinks. In these medicines, the agent for controlling body fat and to be contained in foods and drinks is most preferred.

The above-described functions can be evaluated by known methods, which will be illustrated in the following Experiment Examples.

Experiment Example 1

Preventing action of postprandial increase in blood sugar level:

Alimentary load tests were carried out with 10 healthy male and female adults. The blood sugar level of each subject fasted for at least 4 hours was determined with a device for automatically determining the blood sugar level (Dexter ZII; a product of Bayer Medical Ltd.) before the start of the tests. Then the subjects were given 211 g of Oyako Donburi (a bowl of rice with chicken and eggs) (Ezaki Glico Co., Ltd.; trade name: DONBURI-TEI Kyoto Oyako-Don having energy of 150 kcal. and comprising 13.8 g of protein, 4.8 g of lipid, 13.2 g of carbohydrate and 1402 mg of sodium), 300 g of cooked rice (Sato Food Industries Co. Ltd.; Trade name: Satou no Gohan having energy of 453 Kcal. and comprising 6.9 g of protein, 1.8 g of lipid, 102 g of carbohydrate and 9 mg of sodium) and 8 g of shibazuke (assorted vegetables hashed and pickled in salt) (SHIN-SHIN FOODS Co., Ltd.; having energy of 4 kcal. and comprising 0.1 g of protein, 0.1 g of lipid, 0.6 g of carbohydrate and 0.152 mg of sodium) as load foods together with the test sample within about 10 minutes. 30, 60 and 120 minutes after taking them, the blood sugar level of each subject was determined. The three kinds of test samples were as follows: (1) a tea drink (as control), (2) a tea drink (containing the hydrogenated, hardly digestible dextrin) prepared by adding 5 g, in terms of hardly digestible component, of hydrogenated, hardly digestible dextrin (as the hydrogenated, hardly digestible dextrin) to the control and (3) a tea drink (containing the hardly digestible dextrin) prepared by adding 5 g, as the hardly digestible component, of non-hydrogenated, hardly digestible dextrin to the control. The order of the intake of the foods was at random. The intake tests were carried out by the crossover method while keeping the contents of the samples secret from the subjects. The experimental results were shown by "the average±standard deviation". Determination of statistical significance was done against control, respectively, with paired t-test and significant level in two-sided test was set as 5% of risk level.

As a result, the highest blood sugar level of the subjects who had taken any of the test substances was observed 30 minutes after the meal and then the blood sugar level lowered in all the cases. The average blood sugar level determined 30 minutes after taking the hydrogenated, hardly digestible dextrin was 153.2 mg/dL and that determined 30 minutes after taking a tea drink containing the hardly digestible dextrin was 155.1 mg/dL, while the average level determined 30 minutes after taking the control was 166.4 mg/dL. As compared with the blood sugar level of the group to which the control was given, the level of the groups was significantly lower. The action of the hydrogenated, hardly digestible dextrin in preventing or controlling the blood sugar level after meals could be confirmed (FIG. 1).

Experiment Example 2

Controlling action of intestinal function, maintaining and improving action of sugar resistance, controlling action of the body fat and controlling action of serum lipids (total cholesterol in serum and neutral fat in serum)

Eighteen male Sprague-Dawley rats (Jcl. SD: CLEA Japan, Inc.) (3-week old) were previously given a powdery synthetic feed (hereinafter referred to as "high-sucrose feed) comprising 64.75% of sucrose, 25% of casein, 5% of corn oil, 4% of a mineral mixture (MM-2), 1% of a vitamin mixture (Haeper), 0.2% of choline chloride and 0.05% of vitamin E for 2 weeks. Then the rats were divided into 3 groups each comprising 6 rats. A feed having a high sucrose content was given to rats in group I (hereinafter referred to as "high-sucrose feed group") for 8 weeks. A feed comprising 95% of high-sucrose feed and 5% of the hydrogenated, hardly digestible dextrin was given to the rats in group II and a feed comprising 95% of high-sucrose feed and 5% of the hardly digestible dextrin was given to the rats in group III for 8 weeks. In a normal control group, a normal solid feed for a long term growing (CE-2: CLEA Japan, Inc.) was preliminarily given to 3-weeks old rats for 2 weeks and then the solid feed was continuously fed to them for 8 weeks.

After the growing period of 8 weeks, the following measurements were conducted for evaluating the controlling action of intestinal function, maintaining and improving action of sugar resistance, controlling action of the body fat and controlling action of serum lipids (total cholesterol in serum and neutral fat in serum), of the hydrogenated, hardly digestible dextrin:

(1) The whole feces excreted in 2 days were collected and weighed.

(2) For evaluating the glucose tolerance, the rats were fasted for at least 16 hours and oral saccharide load test, wherein an aqueous solution of 0.75 g/kg of maltodextrin was orally given to the rats, was conducted. The blood was taken from the tail vein without anesthesia before the administration and 30, 60 and 120 minutes after the administration. The blood sugar level was determined with an automatic blood sugar level-measuring device (Dexter ZII: a product of Bayer Medical Ltd.).

(3) The rats were sacrificed by drawing the blood from the abdominal aorta under anesthesia with ethyl ether, and then the fat surrounding the testis, fat surrounding the intestinal tract and the fat in the abdominal cavity were determined.

(4) The blood taken from the abdominal aorta in the course of the dissection was centrifuged and then the total cholesterol in the serum and neutral fat were determined.

In the cases wherein the high-sucrose food was given, the amount of the feces was reduced (average amount of feces: 0.9 g) because the food was free of dietary fibers. Thus, the amount of the feces was significantly smaller than the average amount of feces (9.2 g) in the normal food group. The average amount of feces in the group of rats to which hydrogenated, hardly digestible dextrin was given was 2.8 g. In this group, the amount of feces was larger than that in the group of the rats to which the high-sucrose food was given, though it is smaller than that of the rats to which the normal food was given, and the controlling action of intestinal function could be expected (FIG. 2).

Because the high-sucrose foods do not contain the dietary fibers but contain sucrose (i.e. simple sugar) as the main component, the glucose tolerance is deteriorated and, on the contrary, increase in the serum lipid and accumulation of the body fat are recognized after the intake of the foods for a long period of time. It was reported that such a disorder in the dietary habits causes a pathological sign of diseases caused by the living habits. In these experiments, serious reduction of glucose tolerance, increase in serum lipid and accumulation of body fat were observed/found in the rats in the high sucrose group as compared with those in the normal food group.

FIG. 3 shows the blood sugar curves after the saccharide load in each group. As compared with the blood sugar curve of the normal food group (144.8 mg/dL after 30 minutes, 142.1 mg/dL after 60 minutes and 103.9 mg/dL after 120 minutes), that of the high saccharide group (184.3 mg/dL after 30 minutes, 165.9 mg/dL after 60 minutes and 117.1 mg/dL after 120 minutes) was significantly high. Thus, a serious reduction in the glucose tolerance was observed/found. On the other hand, the blood sugar level in the hydrogenated, hardly digestible dextrin group was 147.3 mg/dL after 30 minutes, 149.8 mg/dL after 60 minutes and 109.4 mg/dL after 120 minutes. In this group, the blood sugar level was always significantly lower than that in the high sucrose feed group. The glucose tolerance in this group was recovered and no difference in the glucose tolerance from the normal food group was recognized.

FIG. 4 shows the results of the determination of the total cholesterol in the serum (FIG. 4a) and neutral fat (FIG. 4b). The serum lipid in the high sucrose feed group (total cholesterol: 91.3 mg/dL, neutral fat: 144.3 mg/dL) was significantly increased as compared with that in the normal feed group (total cholesterol: 62.4 mg/dL, neutral fat: 63.1 mg/dL). However, the serum lipid in the hydrogenated, hardly digestible dextrin group (total cholesterol: 68.6 mg/dL, neutral fat: 86.7 mg/dL) was significantly lower than that in the high sucrose feed group and no significant difference thereof from that of the normal feed group was recognized.

As for the influence on the body fat, the amount of fat at each of the three portions, i. e. fat surrounding the testis (FIG. 5a), fat surrounding the intestinal tract (FIG. 5b) and the fat in the abdominal cavity (FIG. 5c), was determined to find that at all the portions, the amount of the body fat was significantly larger in the high sucrose feed group than that in the normal feed group. Namely, the accumulation of the body fat was recognized in the former group. On the other hand, in the hydrogenated, hardly digestible dextrin group, the amount of the body fat in all the portions was significantly smaller than that in the high sucrose feed group. Thus, the effect of controlling the accumulation of the body fat was recognized in the hydrogenated, hardly digestible dextrin group.

The following Examples will illustrate the compositions of foods having health benefits or enriched with health benefits.

As the hydrogenated, hardly digestible dextrin, Fibersol 2H was used in Examples 2 to 11 and Fibersol 2HL was used in Examples 1 and 12.

Example 1

A carbonated drink (for 5 people) was prepared according to a recipe shown in Table 1.

TABLE 1

| Starting materials | Amount (g) |
| --- | --- |
| Hydrogenated, hardly digestible dextrin (70 wt. % solution) | 70 |
| Granulated sugar | 125 |
| Citric acid | 1.5 |
| Sodium citrate | 0.1 |
| Vitamin C | 0.15 |
| Soda pop essence | 1 |
| Carbonated water | 520 |
| Water | 365 |

Example 2

A jelly (for two people) was prepared according to a recipe shown in Table 2.

TABLE 2

| Starting materials | Amount (g)) |
| --- | --- |
| Gelatin | 10 |
| Water | 280 |
| Sugar | 69 |
| Fruit juice | 150 |
| Hydrogenated, hardly digestible dextrin | 10 |

Example 3

According to the recipe shown in Table 3, water was added to agar powder and then they were heated to obtain a solution. Sugar and hydrogenated, hardly digestible dextrin were dissolved in the solution. The resulting solution was boiled. A red non-sweetened bean jam was added to the solution and the obtained mixture was boiled down to a predetermined quantity. The obtained product was divided into parts (100 g for each person) and then cooled to solidify it in order to obtain soft sweet jellied bean paste.

TABLE 3

| Starting materials | Amount (g) |
| --- | --- |
| Red non-sweetened bean jam | 30 |
| Sugar | 20 |
| Powdered agar | 0.36 |
| Water | 30.64 |
| Hydrogenated, hardly digestible dextrin | 6 |

Example 4

Cookies (for 5 to 10 people) were prepared according to the recipe shown in Table 4 by an ordinary method.

TABLE 4

| Starting materials | Amount (g) |
| --- | --- |
| Wheat flour | 100 |
| Sugar | 40 |
| Hydrogenated, hardly digestible dextrin | 40 |
| Shortening | 45 |
| Water | 25 |

Example 5

Only the egg white was whipped up and then the obtained whip was mixed with other components according to the recipe shown in Table 5. The obtained dough was baked in an oven at 180° C. for 50 minutes to obtain a sponge cake (for 2 or 3 people).

TABLE 5

| Starting materials | Amount (g) |
| --- | --- |
| Refined white sugar | 20 |
| Hydrogenated, hardly digestible dextrin | 15 |
| Egg | 35 |
| Weak flour | 20 |
| Starch syrup | 7 |
| Water | 3 |

Example 6

According to the recipe shown in Table 6, bitter chocolate and cacao butter were molten and then the ingredients other than lecithin were kneaded in the obtained melt and the mixture was refined with a roller mill. Lecithin was added to the mixture and they were tempered to obtain a chocolate (for 2 or 3 people).

TABLE 6

| Starting materials | Amount (g) |
| --- | --- |
| Powdered sugar | 35 |
| Hydrogenated, hardly digestible dextrin | 15 |
| Bitter chocolate | 20 |
| Cacao butter | 15 |
| Powdered milk | 14.7 |
| Lecithin | 0.3 |

Example 7

The starting materials shown in Table 7 were mixed, stirred and beaten enough. Then the obtained dough was fed into cake molds and baked at 180° C. for 30 minutes to produce sponge cakes (for 2 or 3 people).

TABLE 7

| Starting materials | Amount (g) |
| --- | --- |
| Weak flour | 28 |
| The yolk and white of egg | 28 |
| Sugar | 20 |
| Hydrogenated, hardly digestible dextrin | 17.3 |

TABLE 7-continued

| Starting materials | Amount (g) |
| --- | --- |
| Emulsifying agent | 1.3 |
| Water | 5.3 |

Example 8

Sugar and hydrogenated, hardly digestible dextrin were dissolved in the yolk and white of egg. Milk and the flavor were added to the obtained solution. After stirring, the mixture was baked at 160° C. for 30 minutes to obtain pudding(s) (for one person or two people).

TABLE 8

| Starting materials | Amount (g) |
| --- | --- |
| Milk | 68.4 |
| The yolk and white of egg | 10 |
| Sugar | 10 |
| Hydrogenated, hardly digestible dextrin | 11.4 |
| Flavor | A small amount |

Example 9

The whole ingredients were mixed together according to the recipe in Table 9. The obtained mixture was heated at 80° C. to obtain a solution, which was homogenized, then aged for 24 hours and cooled at −40° C. to obtain an ice cream (for one person).

TABLE 9

| Starting materials | Amount (g) |
| --- | --- |
| Fresh cream | 8.4 |
| Butter | 4.2 |
| Sweetened condensed milk | 19.2 |
| Skim milk powder | 2.3 |
| Sugar | 2.5 |
| Hydrogenated, hardly digestible dextrin | 5 |
| Emulsified stabilizer | 0.7 |
| Vanilla flavor | 0.1 |
| Water | 57.6 |

Example 10

All the starting materials were mixed together according to the recipe shown in Table 10. The mixture was boiled down in an enameled pan at 82° C. while the fresh strawberries were ground to obtain a strawberry jam (for 5 people).

TABLE 10

| Starting materials | Amount (g) |
| --- | --- |
| Fresh strawberries | 40 |
| Sugar | 30 |
| Hydrogenated, hardly digestible dextrin | 25 |
| Pectin | 1 |
| Citric acid | 0.3 |
| Water | 3.7 |

Example 11

Rice was cooked according to the recipe shown in Table 11. The rice weighed 295.5 g before cooking and 264.59 g after cooking. The hydrogenated, hardly digestible dextrin content of 180 g of the cooked rice (for one person) was 5.094% by weight.

TABLE 11

| Starting materials | Amount (g) |
| --- | --- |
| Immersed rice (100 g of uncooked rice was immersed in water for 20 minutes) | 128 |
| Hydrogenated, hardly digestible dextrin | 7.5 |

Example 12

A sweetening agent (for 4 or 5 people) was prepared according to the recipe shown in Table 12.

TABLE 12

| Starting materials | Amount (g) |
| --- | --- |
| Reduced maltose syrup (75 wt. % solution) | 65 |
| Hydrogenated, hardly digestible dextrin (70 wt. % solution) | 34.45 |
| Sodium saccharin | 0.55 |

BRIEF DESCRIPTION OF THE DRAWINGS

FIG. 3 is a graph showing the blood sugar level of rats raised with the high-sucrose feed containing hydrogenated, hardly digestible dextrin for 8 weeks and then fasted for 16 weeks as compared with the level of rats raised with the high-sucrose feed free from the hydrogenated, hardly digestible dextrin or with the level of rats raised with the normal feed.

Figure 1:
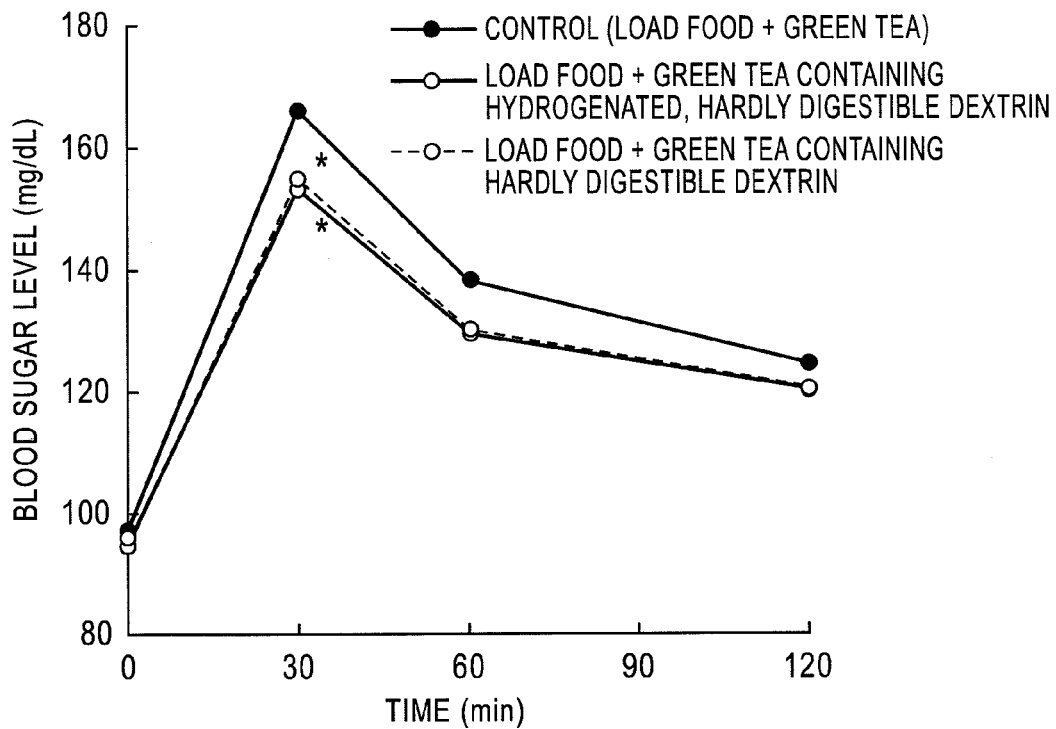
FIG. 1 is a graph showing the comparison in the change in the blood sugar level of healthy subjects after meals between a case in which hydrogenated, hardly digestible dextrin was taken during meals and a case in which it was not taken.
Figure 2:
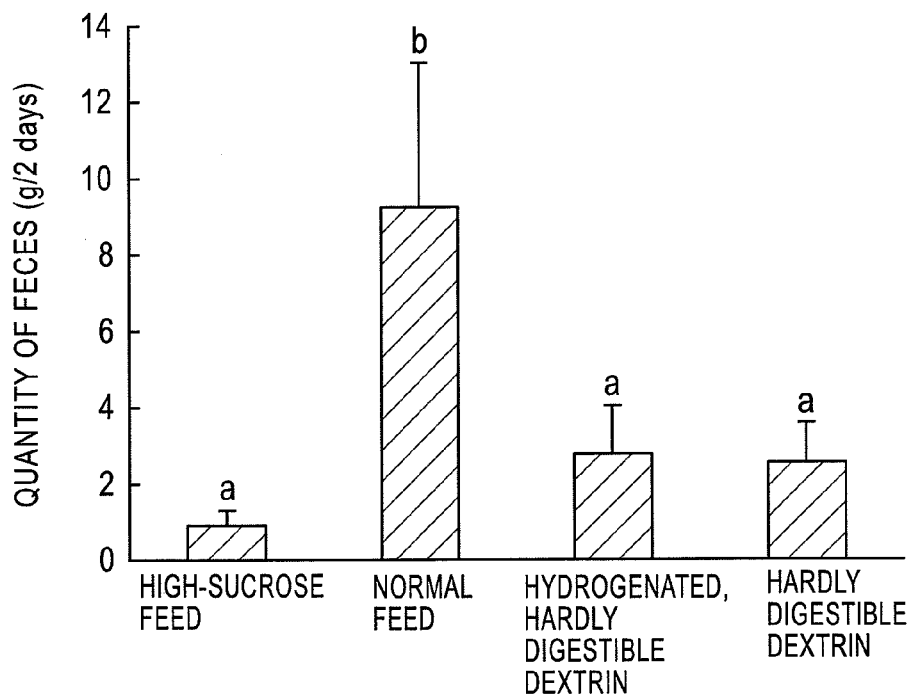
FIG. 2 is a graph showing the amount of feces (2 days) of rats raised with a high-sucrose feed containing hydrogenated, hardly digestible dextrin for 8 weeks as compared with that of rats raised with only the high-sucrose feed or with that of rats raised with a normal feed.
Figure 4A:
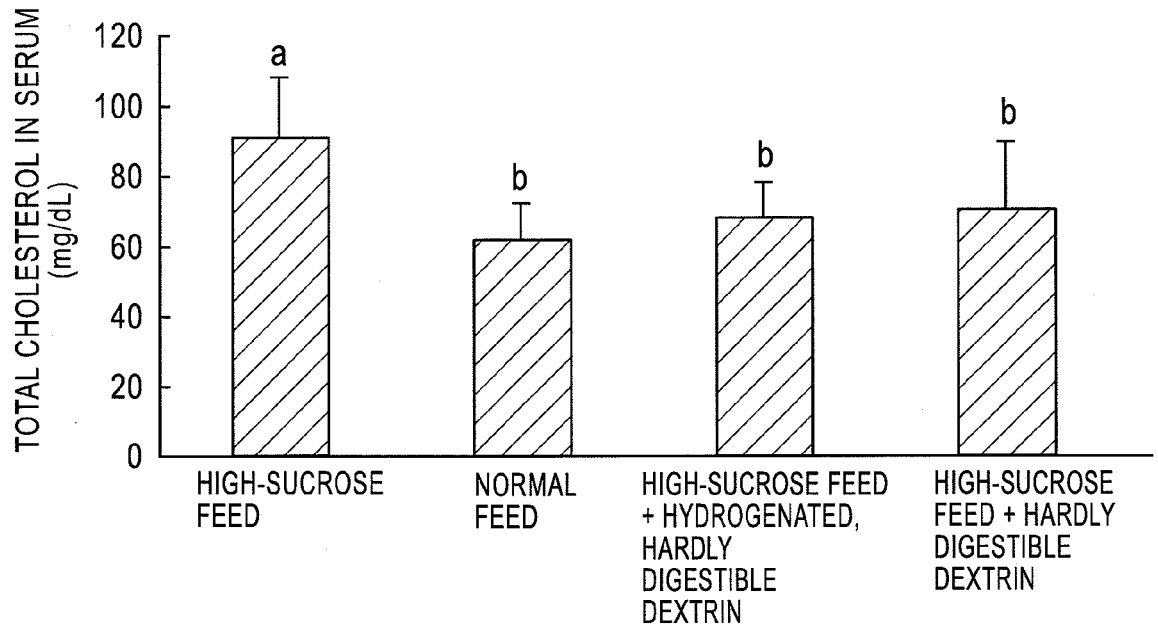
FIG. 4 is a graph showing the total cholesterol in the serum (FIG. 4*a*) and neutral fat in the serum (FIG. 4*b*) of rats raised with the high-sucrose feed containing the hydrogenated, hardly digestible dextrin for 8 weeks as compared with the results of rats raised with the high-sucrose feed free from the hydrogenated, hardly digestible dextrin or rats raised with the normal feed.
Figure 4B:
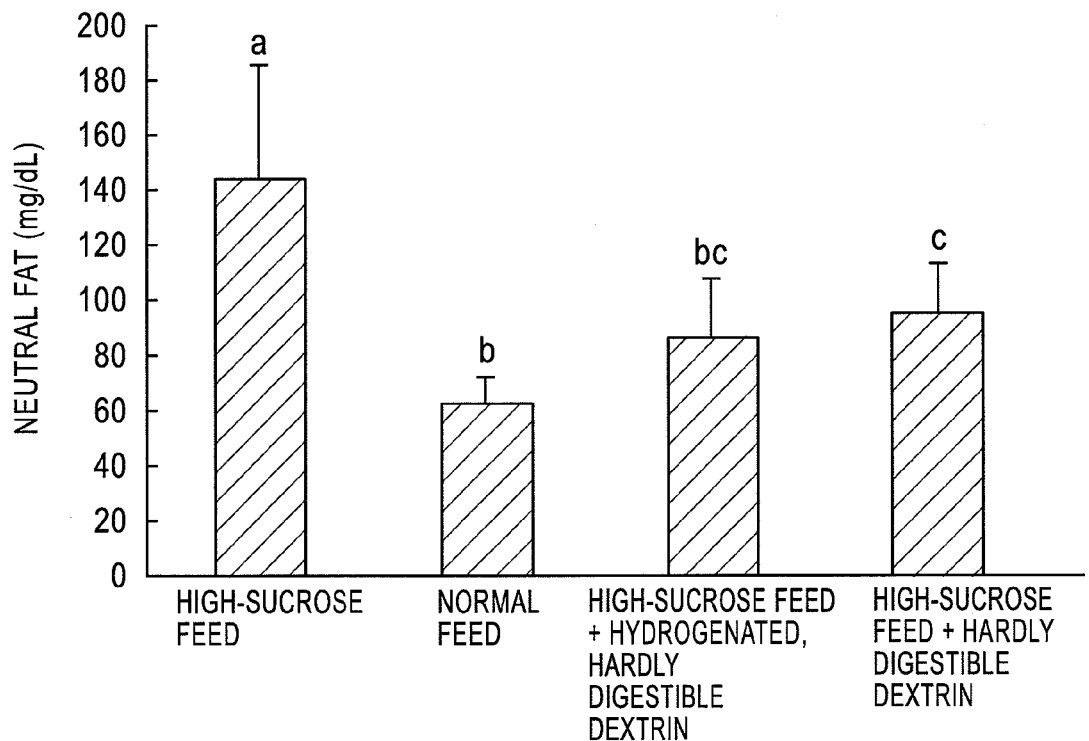
Figure 5A:
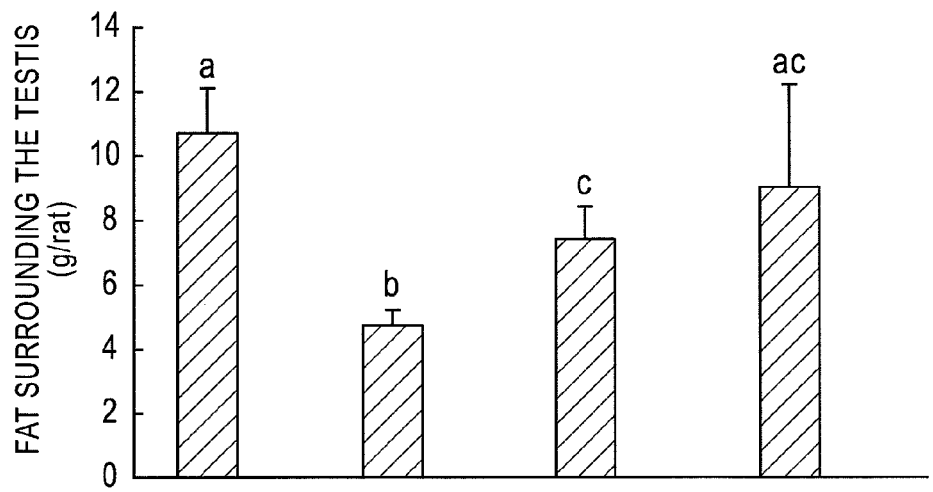
FIG. 5 is a graph showing the amount of each of the fat surrounding the testis (FIG. 5*a*), the fat surrounding the intestinal tract (FIG. 5*b*) and the fat in the abdominal cavity (FIG. 5*c*) of rats raised with the high-sucrose feed containing the hydrogenated, hardly digestible dextrin for 8 weeks as compared with the results of rats raised with the high-sucrose feed free from the hydrogenated, hardly digestible dextrin or rats raised with the normal feed.
Figure 5B:
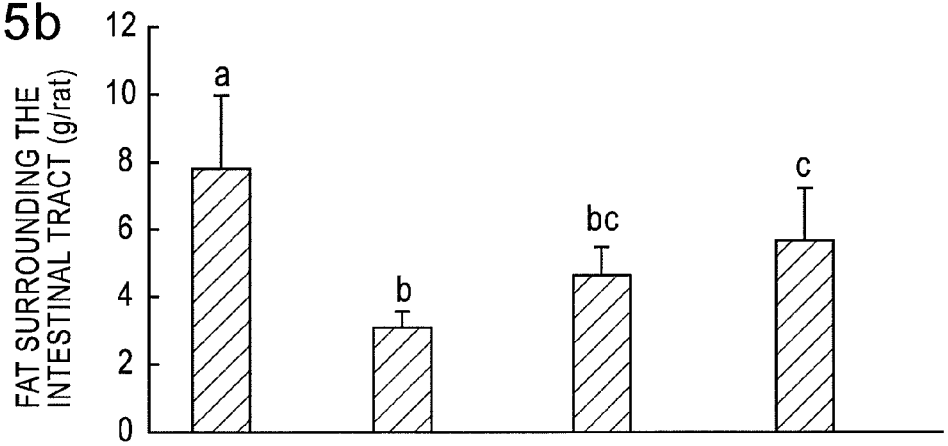
Figure 5C:
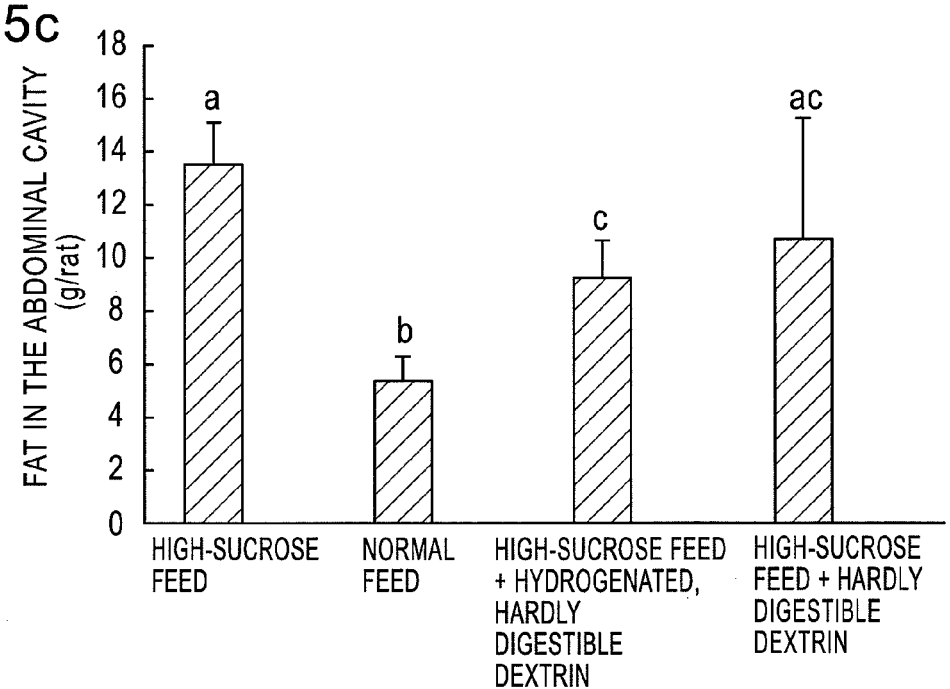

What is claimed is:

1. A method for lowering the accumulation of body fat in human or animal by intaking an effective amount of foods or drinks, wherein the foods and drinks comprise as an active ingredient a hydrogenated, indigestible dextrin that is obtained by digesting pyrodextrin with α-amylase and glucoamylase to obtain an indigestible dextrin, and then hydrogenating the indigestible dextrin.

2. A method for lowering the accumulation of body fat in human or animal by intaking an effective amount of foods or drinks, wherein the foods and drinks comprise as an active ingredient a hydrogenated, indigestible dextrin that is obtained by digesting pyrodextrin with α-amylase and glucoamylase to obtain an indigestible dextrin, and then hydrogenating the indigestible dextrin; and
    wherein an amount of the hydrogenated, indigestible dextrin is at least 3 g/day.

* * * * *